(12) United States Patent
Nakama et al.

(10) Patent No.: US 6,323,246 B1
(45) Date of Patent: *Nov. 27, 2001

(54) COMPLEX AND EMULSIFIED COMPOSITION

(75) Inventors: Yasunari Nakama; Michihiro Yamaguchi; Kiyoshi Miyazawa; Takayuki Ohmura, all of Yokohama (JP)

(73) Assignee: Shiseido Company, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,375

(22) Filed: Sep. 16, 1998

Related U.S. Application Data

(62) Continuation of application No. 08/281,497, filed on Jul. 27, 1994, now Pat. No. 5,866,040, which is a continuation of application No. 07/834,525, filed as application No. PCT/JP91/00807 on Jun. 15, 1991, now abandoned.

(30) Foreign Application Priority Data

Jun. 15, 1990 (JP) .................................... 2-157257
Jun. 11, 1991 (JP) .................................... 3-166367

(51) Int. Cl.$^7$ .............................. B01F 17/28; B01F 3/08; C07C 229/10

(52) U.S. Cl. ................. 516/27; 516/54; 516/69; 516/915; 514/939; 514/943; 424/70.19; 424/70.21; 554/63; 568/553; 510/123; 510/437

(58) Field of Search ............................ 516/27, 54, 69, 516/203, 915; 514/939, 943; 424/70.19, 70.21; 554/103, 52, 63; 562/108, 114, 553; 510/123, 437, 480, 494

(56) References Cited

U.S. PATENT DOCUMENTS 3,520,818  7/1970  Cambre .............................. 510/398
3,590,122  6/1971  Roberts et al. ..................... 424/70.19

(List continued on next page.)

FOREIGN PATENT DOCUMENTS 1 548 948  12/1967  (JP) .

(List continued on next page.)

OTHER PUBLICATIONS

Myers, Surfactants Science and Technology (1992 VHC Publishers, NY, NY, copyright 1992 month unknown) pp. 232–241.*

(List continued on next page.)

Primary Examiner—Daniel S Metzmaier
(74) Attorney, Agent, or Firm—Norris McLaughlin & Marcus

(57) ABSTRACT

A fatty acid amphoteric surfactant complex obtained by mixing a) at least one imidazolinium ampholytic surfactant of the formula:

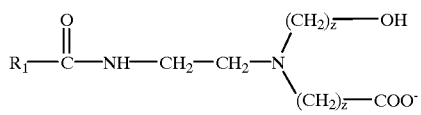

wherein
 $R_1$ represents an alkyl or alkenyl group having 9 to 17 carbon atoms on average; and
 Z is 1 or 2;
with b) a higher fatty acid selected from the group consisting of oleic acid, isostearic acid and a mixture of oleic acid and isostearic acid;
wherein the ratio of said higher fatty acid to the total amount of said imidazolinium ampholytic surfactant(s) in said complex ranges from about 25:75 to 90:10. The complex containing an ampholytic and/or semipolar surfactant and higher fatty acid may optionally contain a clay mineral. Said complex may be employed in making emulsions.

22 Claims, 2 Drawing Sheets

U.S. PATENT DOCUMENTS

| | | | |
|---|---|---|---|
| 4,165,293 | 8/1979 | Gordon | 510/147 |
| 4,329,335 | 5/1982 | Su et al. | 424/70.19 |
| 4,337,241 | 6/1982 | Ser et al. | 424/59 |
| 4,436,637 | 3/1984 | Ramachandran et al. | 510/328 |
| 4,511,513 | 4/1985 | Guth et al. | 510/123 |
| 4,830,782 | 5/1989 | Broze et al. | 510/304 |
| 4,900,467 | 2/1990 | Smith | 510/195 |
| 4,913,828 | 4/1990 | Caswell et al. | 510/297 |
| 5,204,010 | 4/1993 | Klewsaat | 510/527 |
| 5,354,906 | 10/1994 | Weitemeyer et al. | 554/52 |
| 5,866,040 * | 2/1999 | Nakama et al. | 516/22 |

FOREIGN PATENT DOCUMENTS

| | | |
|---|---|---|
| 49 48843 | 9/1972 | (JP) . |
| 53 103987 | 9/1978 | (JP) . |
| 54 6593 | 3/1979 | (JP) . |
| 58 38480 | 8/1983 | (JP) . |
| 60 49099 | 7/1984 | (JP) . |

OTHER PUBLICATIONS

Abstract of JP 63 308097 Dec. 15, 1988 (Kanebo LTD), Patent Abstracts of Japan, 62 C 584.

Abstract of JP 61 271029 Dec. 1, 1986 (Kanebo Ltd), Patent Abstracts of Japan, 117 C 418.

Abstract of JP 60 222142 Nov. 6, 1985 (Shiseido K.K.), Patent Abstracts of Japan, 106 C 237.

Abstract of JP 60 197614 Oct. 7, 1995 (Shionogi Seiyaky K.K.), Patent Abstracts of Japan, 10 C 331.

Abstract of JP 2 49713 Feb. 20, 1990 (Shiseido Co. LTD), Patent Abstracts of Japan, 90 C 716.

Abstract of JP 55 129141 Oct. 10, 1980 (Rowaaru Keshiyouhin K.K.), Patent Abstracts of Japan, 72 C 37.

Abstract of JP 59 19673 Aug. 11, 1984 (Raion K.K.), Patent Abstracts of Japan, 105 C 720.

Abstract of JP 2 59511 Feb. 28, 1990 (Shiseido Co. LTD), Patent Abstracts of Japan, 47 C 720.

Abstract of JP 61 155 310 (Lion Corp.), Patent Abstracts of Japan, Section C, Sect. #388, vol. 10, #355, p. 121, (Nov. 1986).

Derwent, AN 82–5624E and JP 57 087 499 (Lion Corp.), Derwent week 8227.

Derwent, AN 88 21593 and JP 63 150 221 (Shiseido K.K.), Derwent Week 8831.

Kokichi Hikime and others "Handobod–Cosmetics–Preparation Material—revised Edition", Feb. 1, 1977, Nikko Chemicals, Tokyo, pp. 336–345, (Translation–None).

"Communications pursuant to Article 96(2) and Rule 51(2) EPC" from the European Patent Office, Appln. No. 91911083.3, 3 pages, (Aug., 1991).

The Merck Index, An Encyclopedia of Chemicals, Drugs, and Biologicals, Tenth Edition, (Merck & Co., Inc., Rahway, N.J. 1983) Month unknown p. 1299.

* cited by examiner

COMPLEX AND EMULSIFIED COMPOSITION

This is a continuation of application Ser. No. 08/281,497, filed on Jul. 27, 1994, now U.S. Pat. No. 5,866,040, which is a continuation of application Ser. No. 07/834,525, filed on Feb. 3, 1992, now abandoned. Application Ser. No. 07/834,525 is filed under 35 USC 371 and based on PCT/JP91/00807, filed Jun. 15, 1991 now abandoned.

TECHNICAL FIELD

The present invention relates to a novel complex and an emulsified composition, and more specifically, to a novel complex obtained by mixing an ampholytic surfactant and/or a semi-polar surfactant (hereinafter referred to as "ampholytic surfactant, etc.") and a higher fatty acid, as well as an emulsified composition comprising the novel complex and being easily prepared, having an emulsification type selectable from an O/W type to a W/O type, and exhibiting little irritation of the skin.

BACKGROUND ART

In general, when preparing an emulsified product, a nonionic surfactant or an ionic surfactant is used as an emulsifier.

Nevertheless, because the oily substance to be emulsified exhibits various polarities, to obtain a stable emulsified substance, a measure of first obtaining the degree of polarity (the "required HLB") of the oily substance and then selecting a surfactant in conformity with that degree of polarity before using the agent, is taken. As the emulsifier, in many cases a hydrophilic emulsifier with a high HLB value and a lipophilic emulsifier with a low HLB value are combined with one another.

As a lipophilic emulsifier with a high HLB value, e.g., anionic surfactants such as fatty acid soap and alkylsulfuric ester salt; cationic surfactants such as distearyldimethylammonium chloride and stearyltrimethylammonium chloride; and nonionic surfactants having a long polyoxyethylene chain length, e.g., polyoxyethylene alkylether, polyoxyethylene fatty ester and polyoxyethylene sorbitan fatty ester, are used.

Further, as a lipophilic emulsifier with a low HLB value, e.g., a nonionic surfactant with a short polyoxyethylene chain, sorbitan fatty esters and glycerine fatty esters are used.

The required HLB value of an oily substance to be emulsified is obtained by using a nonionic surfactant having an already known HLB value. Very complex means are required for obtaining the required value, e.g., the ratio of the amounts of a surfactant with a high HLB and a surfactant with a low HLB is varied. Further, an emulsifier is selected on the basis of the required HLB thus-obtained, and an emulsified product is prepared using this emulsifier. Nevertheless, a stable emulsified product is seldom obtained in practice, and thus experiments must be repeated on a trial and error basis.

To cope with the above problem, it is disclosed that an emulsifier containing an alkanolamine of oleic acid and an anionic surfactant can emulsify a comparatively wide range of HLB (refer to Japanese Unexamined Patent Publication No. 61-114724), but an emulsified product prepared by using the above surfactant as an emulsifier has a drawback in that it has a high skin irritation effect.

Conversely, an ampholytic surfactant is known to exhibit a low skin irritation, and a large number of emulsified products consisting essentially of an ampholytic surfactant, e.g., a low skin irritation detergent composition, or a shampoo composition with a low irritation of the eyes, etc., have been disclosed (refer to the official gazettes of Japanese Unexamined Patent Publication No. 57-90099 and U.S. Pat. No. 3,950,417).

The ampholytic surfactant disclosed in these official gazettes, however, do not exhibit a strong emulsification of an oily substance with a wide range of required HLB, and furthermore, an emulsion type of O/W or W/O is difficult to control and a stable emulsified product can not be formed.

Accordingly, there has not been obtained an emulsifier displaying a strong emulsification of even an oily substance with a wide range of required HLB, capable of easily controlling the emulsification type, and capable of producing a stable emulsified product having a low skin irritation.

DISCLOSURE OF THE INVENTION

An object of the present invention is to provide a novel complex displaying an excellent emulsification of even an oily substance with a wide range of HLB, without the above-mentioned problems of the prior arts, and able to easily control the emulsification type, and able to be used also as an emulsifier able to form a stable emulsified product having a low skin irritation.

Another object of the present invention is to provide an emulsified composition able to be easily prepared even when containing an oily substance with a wide range of required HLB, and having an excellent stability and a low skin irritation.

The other objects and advantages of the present invention will be apparent from the following description.

In accordance with the present invention, there is provided a novel complex obtained by mixing an ampholytic and/or a semi-polar surfactant and a higher fatty acid.

In accordance with the present invention, there is also provided an emulsified composition contained in the above-mentioned novel complex.

BEST MODE OF CARRYING OUT THE INVENTION

Figure 1:
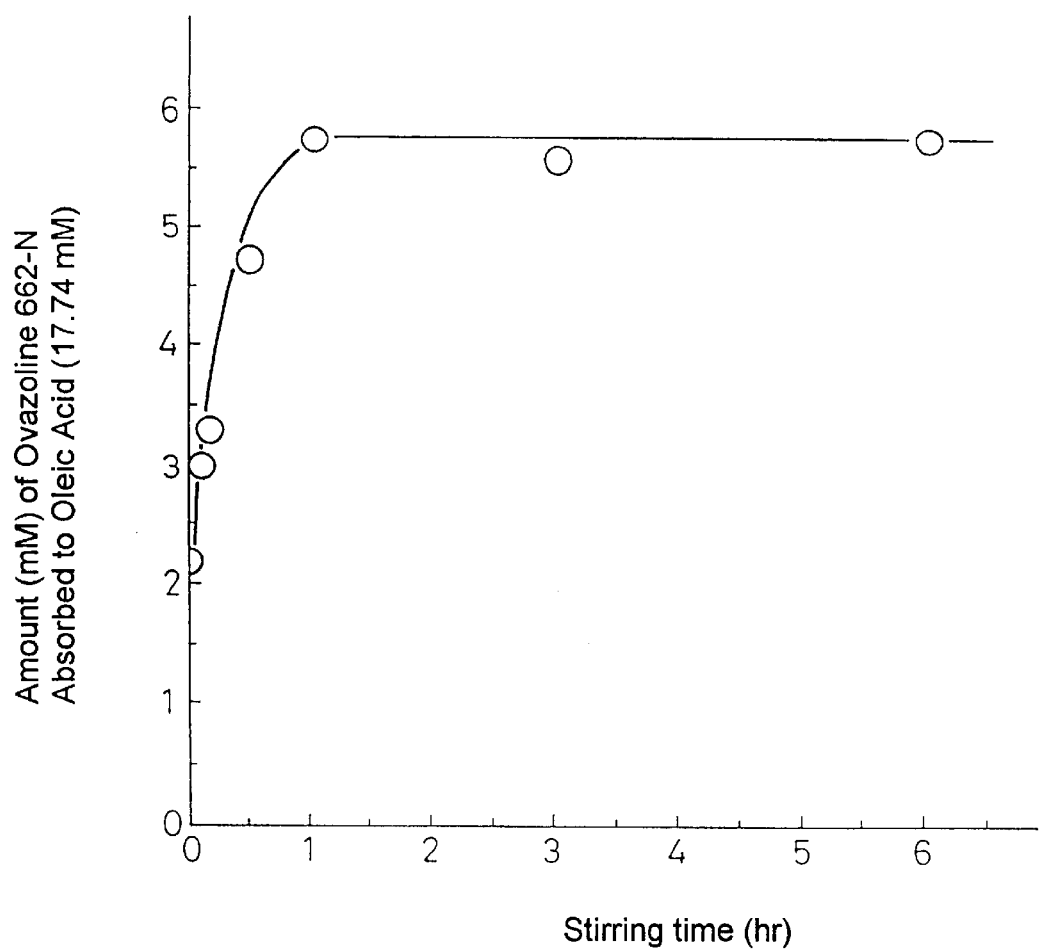
FIG. 1 is a graph showing the variation with time of the amount of a surfactant adsorbed to a higher fatty acid.

Specific and preferred embodiments of the present invention are now explained as follows.

Ampholytic Surfactant and Semi-polar Surfactant

The examples of the ampholytic surfactants used in the present invention include any ampholytic surfactant used for ordinary cosmetic bases Specific examples thereof are as follows.

(A) Amidobetaine ampholytic surface active agents represented by the general formula:

$$R_1-\overset{O}{\overset{\|}{C}}-NH(CH_2)_x-\overset{(CH_2)_yCH_3}{\underset{(CH_2)_yCH_3}{N^+}}-CH_2COO^-$$ (A)

[Corresponding commercially available products are, e.g., "Lebon 2000" (produced by Sanyo Kasei K.K.) and "Anon BDF" (produced by Nihon Yushi K.K.)]

(B) Amidosulfonebetaine ampholytic surfactants represented by the general formula:

$$R_1-\overset{O}{\overset{\|}{C}}-NH(CH_2)_x-\overset{(CH_2)_yCH_3}{\underset{(CH_2)_yCH_3}{N^+}}-CH_2CH_2CH_2SO_3^-$$ (B)

[Corresponding commercially available products are, "Ronzaine-CS" (produced by Ronza) and "Milataine CBS" (produced by Milanol]

(C) Betaine ampholytic surfactants represented by the general formula:

$$R_2-\overset{(CH_2)_yCH_3}{\underset{(CH_2)_yCH_3}{N^+}}-CH_2COO^-$$ (C)

[Corresponding to, e.g., "<u>Anon</u> BL" (produced by Nihon Yushi K.K. and Dehainton AB-30 (produced by Henkel) as commercially available products]

(D) Sulfobetaine ampholytic surfactants represented by the general formula:

$$R_2-\overset{(CH_2)_yCH_3}{\underset{(CH_2)_yCH_3}{N^+}}-(CH_2)_xSO_3^-$$ (D)

[For example, as a commercially available product, Ronzaine 12 CS (produced by Ronza) corresponds thereto]

(E) Imidazolinium ampholytic surfactants represented by the general formula:

$$R_1-\overset{O}{\overset{\|}{C}}-NHCH_2CH_2N\begin{matrix}(CH_2)_z-OH\\ (CH_2)_zCOO^-\end{matrix}$$ (E)

[As commercially available products, e.g., "Ovazoline 662-N" (produced by Toho Kagaku K.K.) and "Anon GLM" (Nihon Yushi K.K.) correspond thereto]

The semi-polar surfactant used in the present invention also includes any semi-polar surface active agent used for ordinary cosmetic bases, etc. Concrete examples thereof are as follows.

(F) Tertiary amine oxide semi-polar surfactants represented by the general formula:

$$R_2-\overset{CH_3}{\underset{CH_3}{N}}-O$$ (F)

[As commercially available products, e.g., "Unisafe A-LM" (produced by Nihon Yushi K.K.) and "Wondamine OX-100 (produced by Shin Nihon Rika K.K.) correspond thereto.]

In the foregoing general formulas (A) to (F), $R_1$ denotes an alkyl or alkenyl group having 9 to 21 carbon atoms on average, an alkyl or alkenyl group having 11 to 17 carbon atoms on average being preferable, an alkyl or alkenyl group having 11 to 13 carbon atoms being most preferable. When the average number of carbon atoms in the group $R_1$ is less than 9, the hydrophilic nature of the group is so strong that a complex is difficult to form, whereas when the average number more than 21, the solubility of the group in water becomes so bad that the group is also difficult to form.

$R_2$ represents an alkyl or alkenyl group having 10 to 18 carbon atoms on average, x is an integer of 2 to 4, y an integer of 0 to 3, and z an integer of 1 or 2.

In the present invention, optionally, one or more of these ampholytic and semi-polar surfactants can be used.

Higher Fatty Acids

As the higher fatty acids used in the present invention, there are mentioned optional higher fatty acids used in ordinary cosmetic bases, etc., and concretely, the higher fatty acids represented by the following general formula (G) are mentioned.

General formula (G):

$$R_3COOH \tag{G}$$

In the above formula, $R_3$ denotes a saturated or unsaturated hydrocarbon radical having 7 to 25 carbon atoms on average with having a straight or branched chain or having a hydroxyl group, a saturated or unsaturated hydrocarbon having 9 to 23 carbon atoms on average with a straight or branched chain or having a hydroxyl group being preferable, and the most preferable being a saturated or unsaturated hydrocarbon having 11 to 21 carbon atoms on average with a straight or branched chain. When the average number of carbon atoms is less than 7, the hydrophilic nature of the higher fatty acid is so strong that a complex is difficult to form, whereas when the average number of carbon atoms is more than 25, the melting point of the higher fatty acid becomes so high that a complex becomes difficult to form.

Specific examples of such higher fatty acid are saturated fatty acids such as lauric acid, myristic acid, stearic acid, palmitic acid, arachic acid, behenic acid, etc.; unsaturated fatty acids such as 2-palmitoleic acid, petroselinic acid, oleic acid, elaidic acid, recinolic acid, linoleic acid, linoelaidic acid, linolenic acid, arachidonic acid etc.; branched fatty acids such as isostearic acid etc.; hydroxycarboxylic acids such as 12-hydoxystearic acid; etc. Among these higher fatty acids, saturated fatty acids having 18 carbon atoms are preferable from the viewpoint of stability and skin irritation, and among them, those having branches are especially preferable, more preferable being saturated fatty acids having 18 carbon atoms and having a methyl branch. As commercially available products of higher fatty acids, there may be mentioned, e.g., isostearic acid ("Emery #871, #875", produced by Emery Co., Ltd.) and so forth. In the present invention, optionally, one or more of these higher fatty acids may be used.

Clay Mineral

As the clay minerals optionally used in the present invention, there are mentioned natural and synthetic water swelling clay minerals such as montmorillonite, zaconite, nontronite, saponite, hectorite, vermiculite, beagum, bentonite, silicate, fluorosilicate, magnesium, aluminium, syntheic hectorite (laponite) etc. Further, in the present invention, organic modified clay minerals obtained by treating these clay minerals with a quaternary ammonium type cationic surface active agent, e.g., Benton-27 (stearyldimethylbenzylammoniumhectorite chloride) and Benton-38 (distearyldimethylbenzylazmmoniumhectorite chloride) can be used.

The preferred amount of an added clay mineral is within the range of from 0.01 to 5% by weight, more preferably from 0.1 to 2% by weight of the total amount of the novel complex. The complex with a clay mineral compounded in an amount within the above range, and an emulsion composition using such complex as an emulsifier, have a more improved stability.

Novel Complex and Process for the Preparation Thereof

The present inventors found that, when an aqueous solution of an ampholytic surfactant or the like and a fatty acid are mixed, a complex insoluble in both water and oil is produced. The novel complex according to the present invention is completely different from an ampholytic and/or semi-polar surfactant and from a higher fatty acid in chemical composition, and is not a mixture thereof. This complex has a melting point of 100° C. or higher, and is combined with the ampholytic and/or semi-polar surfactant at the carboxyl group portion of the higher fatty acid.

The complex according to the present invention can be produced, e.g., in the following manner.

That is, an ampholytic and/or semi-polar surfactant and water are mixed to thereby prepare an aqueous solution of the ampholytic and/or semi-polar surfactant. Next, to the aqueous solution of ampholytic and/or semi-polar surfactant thus prepared, there is added a higher fatty acid. If necessary, it is preferable to effect this addition while agitating with a suitable agitator. When the higher fatty acid is thus added to the ampholytic and/or semi-polar surfactant, the ampholytic and/or semi-polar surfactant(s) adsorbed to the higher fatty acid, and combined to the higher fatty acid at the carboxyl group portion thereof. This adsorption of the ampholytic and/or semi-polar surfactant to the higher fatty acid is increased as time elapses, and is saturated after a predetermined time has elapsed.

When the solution thus obtained after the addition of the higher fatty acid is subjected to, e.g., centrifugal separation, the novel complex according to the present invention is suspended as a solid, so that the complex can be easily separated and recovered.

Further, the emulsion stability of the present invention is superior due to the presence of the clay mineral at the time of production. The clay mineral may be either first dispersed in an aqueous phase or dispersed in an oil phase according to the emulsification type. In the above example, by adding a higher fatty acid with a dispersed clay mineral to an aqueous solution of the ampholytic and/or semi-polar surfactant, a more stable novel complex is obtained.

Uses of Novel Complex

The novel complex according to the present invention may be favorably used, e.g., as an emulsifier.

Namely, when an oily substance is present, this complex is orientated at the interface between water and oil, and functions as a strong interfacial film of the emulsion particle interface, and thus an emulsifier providing a strong emulsification capable of preventing a coalescence of the particles, which is not influenced by fluctuations in the required HLB of the oily substance, is obtained. Furthermore, since the HLB of the complex can be adjusted depending on the mixing ratio of the ampholytic and/or semi-polar surfactant and the higher fatty acid, the emulsification type can be easily selected.

Preparation of Emulsified Composition

The emulsified composition according to the present invention can be prepared by adding the above-mentioned novel complex according to the present invention to an oily substance-containing liquid, if necessary, under agitation and/or heating.

Although it takes 2 to 3 hours to make a stable emulsion system according to a normal method, it takes only one hour when the complex of the present invention is used, and the system can be completely emulsified by propeller agitation or the like, whereby the production process is simplified and shortened.

The emulsified composition also can be prepared according to the under-mentioned process, from the viewpoint of ease of preparation.

Namely, the emulsified composition can be prepared in such a way that a higher fatty acid is added to an oily substance, and the obtained mixture is agitated using, e.g., a disper, at room temperature, when the mixture is liquid at room temperature, and in a melted state under heating when it is solid at room temperature, and an aqueous solution of an ampholytic and/or semi-polar surfactant is added little by little to the mixture while the agitation is continued. When the fatty acid is difficult to dissolve in the oily substance, the emulsification efficiency can be increased by adding a solvent such as isoparaffin to the mixture.

With regard to additive components other than the emulsifier, these components can be added to the emulsified composition promptly after the preparation of the above emulsified composition, and then stirred slightly.

Mixing Ratio and Formulating Amount

In the present invention, a higher fatty acid and an ampholytic and/or semi-polar surfactant are blended in a blending ratio such that the weight ratio of the former to the latter is preferably within the range of from 0.5:9.5 to 9.5:0.5 {(higher fatty acid)/(ampholytic and/or semi-polar surfactant)=0.05 to 19}, more preferably 1:9 to 9:1 {(higher fatty acid)/(ampholytic and/or semi-polar surfactant)=0.1 to 9}. Such a mixing ratio can be properly set according to the objective emulsion type. When the mixing ratio is set within the range of from 0.5:9.5 to 9.5:0.5, the stability of the emulsified product is improved, and when set within the range of from 1:9 to 9:1, the stability thereof is further improved.

Further, the total amount of the surfactant and the higher fatty acid is preferably within the range of from 0.1 to 30% by weight, based on the total weight of the composition, more preferably from 0.5 to 20% by weight. When this amount is 0.1% by weight or more, the stability of the emulsified product is improved, and when it is 0.5% by weight or more, the stability thereof is further improved. Nevertheless, when a surfactant and higher fatty acid are contained in the whole composition in a proportion of 30% by weight or more, the effect is saturated, and therefore, the upper limit is preferably 30% by weight, from an economical point of view. Although the emulsification type varies depending upon the kind of oily substance, the proportion between water and oil, etc., the emulsification type is divided into two at roughly a weight ratio of 1 to 2 of the higher fatty acid and the ampholytic and/or semi-polar surfactant; O/W type below a ratio of 1 to 2, and W/O type above this ratio. Also by using a preparation method such as phase reversal emulsifying method, it becomes possible to prepare a stable multiphase emulsified product of, e.g., the W/O/W type or O/W/O type.

Optional Contents

In the emulsified composition of the present invention, if necessary, other surfactants, viscosity regulators, medicative agents, humectants, preservatives, pH regulators, ultraviolet absorbers, etc., can be used in combination with the present novel complex.

As the other surfactant, there are mentioned, e.g., polyoxyethylene alkylether, polyoxyethylene fatty ester, polyoxyethylene sorbitan fatty ester, polyoxyethylene hardened castor oil, alkylsulfuric ester, polyoxyethylene alkylsulfuric ester, alkylphosphoric ester, polyoxyethylene alkylphosphoric ester, alkali metal salts of fatty acids, etc.

As the viscosity regulator, there are mentioned, e.g., high molecular compounds such as polyvinyl alcohol, carboxyvinyl polymer, carboxymethylcellulose, methylcellulose etc.; natural gums such as gelatin, traganth gum, etc.; and alcohols such as ethanol, isopropanol, etc.

As the medicative agent, there are mentioned, e.g., disinfectant, antiphlogistic agent, vitamins, etc.

As the humectant, there are mentioned, e.g., glycerine, propylene glycol, 1,3-butylene glycol, sorbitol, lactic acid, sodium lactate, sodium pyrrolidone carboxylate, etc.

As the preservative, there are mentioned, e.g., paraoxybenzoic ester, benzoic acid, sodium benzoate, sorbic acid, potassium sorbate, phenoxy ethanol, etc.

Emulsified Oily Substance

There is a wide variety, from polar oils to non-polar oils, of the oily substances which can be emulsified with the emulsifier of the present invention, and examples thereof include hydrocarbons such as liquid paraffin, branched chain light paraffin, paraffin wax, ceresin, squalene, etc.; waxes such as beeswax, spermaceti wax, carnauba wax, etc.; natural animal and plant fats and oils such as olive oil, camellia oil, hohova oil, lanolin, etc.; ester oils such as isopropyl myristate, cetyl isooctanoate, glyceryl trioctanoate, etc.; silicone oils such as decamethyl pentasiloxane, dimethyl polysiloxane, methyl phenyl polysiloxane, etc.; and higher alcohols such as cetyl alcohol, stearyl alcohol, oleyl alcohol, etc. These may be used alone or as a mixture of two or more thereof. Further, among the above oily substances, a high viscosity silicone can be formed into a product with service properties similar to those of a W/O type emulsion, although the product is an O/W type.

Uses of Emulsified Composition

The emulsified composition according to the present invention may be applied, as cosmetics, to skin care products such as cold cream, cleansing cream, etc.; hair care products such as hair cream, hair shampoo, hair mousse, hair rinse, etc.; makeup products such as foundation (face powder, powder), rouge, eye makeup (mascara, etc.), etc.; body products, fingernail treatment cosmetics, etc. In addition, the present emulsified composition may be effectively used in a wide range of industrial fields such as releasing agents, water repellents, water-proofing agents, and pharmaceuticals and agricultural chemicals.

EXAMPLES

The present invention is now explained in detail with reference to Examples, which in no way limit the present invention.

Example 1

As an ampholytic surfactant, Ovazoline 662-N was used (10 mM), and as a higher fatty acid, oleic acid (17.73 mM) was used.

The latter was added to the former, and the mixture was agitated with a stirrer, and then the mixture was subjected to a centrifugal separation treatment. The amount of the Ovazoline 662-N remaining as sediment was measured using HPLC (High Performance Liquid Chromatography), to confirm whether the Ovazoline 662-N was adsorbed to oleic acid as time elapsed.

The results are shown in FIG. 1.

It can be seen from FIG. 1 that Ovazoline 662-N was reduced in amount as time elapsed, and adsorbed to oleic acid to form a complex.

Figure 2:
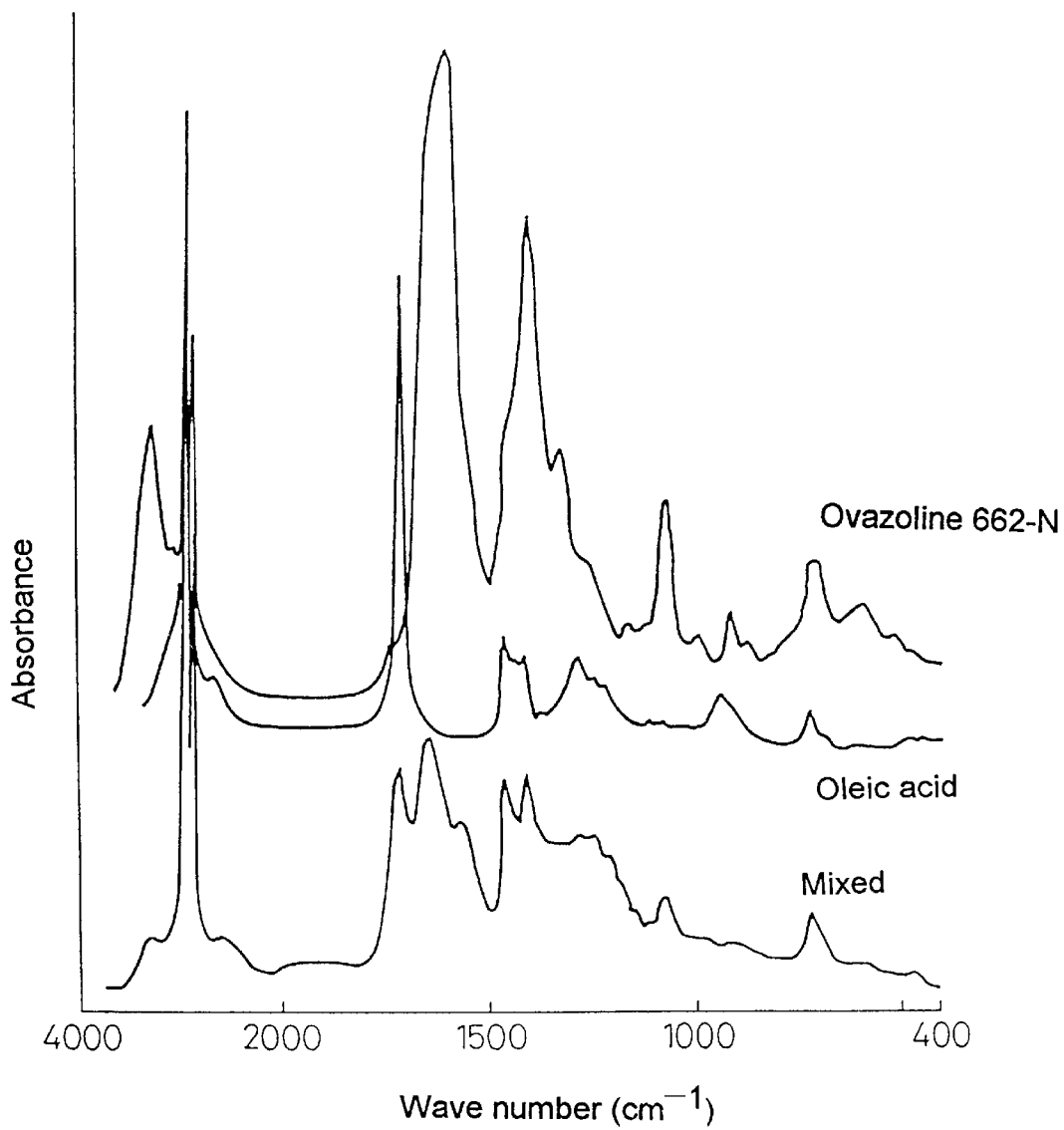
FIG. 2 is an infrared adsorption spectrum diagram of the novel complex.

Furthermore, the results of a measurement of the IR (Infrared Absorption Spectrum) for this system are shown in FIG. 2. It can be seen from FIG. 2 that the signal pattern of the complex was different from the superposition of the signal patterns of each component of the complex. Also, from the fact that the signal near a number of waves of 940 $cm^{-1}$ for —OH of oleic acid vanishes., after mixing both components, it can be seen that oleic acid is combined with Ovazoline 662-N in the carboxyl group portion of oleic acid.

From the foregoing results, it can be seen that the complex consisting of the ampholytic surface active agent and the fatty acid is a substance entirely different from these two components.

The melting point of this complex was determined and found to be 100° C. or more.

Examples 2 to 11 and Comparative Examples 1 to 5

According to the foregoing procedures, the emulsified compositions with the compositions as set forth in Table 1 were prepared.

Aqueous solutions of anionic, ampholytic and nonionic surfactants dissolved in purified water were stirred in a homogenizer, and to each solution thus obtained was added an oil in which a fatty acid was dissolved, whereby an emulsified product was prepared.

In Examples 4 and 5, the emulsification type was adjusted by phase inversion emulsifying method, i.e., the oil with a fatty acid dissolved therein was stirred in a homogenizer, and an aqueous solution of an ampholytic surfactant was added to the mixture thus homogenized, whereby an emulsified product was prepared.

The stability, emulsification type and skin irritation of the emulsified composition prepared as mentioned above were evaluated as follows.

Stability of Emulsified Composition

After the emulsified composition had been allowed to stand for one month at room temperature, the size of the emulsified particles was compared with that of the particles immediately after the preparation of the emulsified composition, whereby the stability of the emulsified composition was evaluated according to the following criterion.

○ . . . No coalescence of particles recognized.

Δ . . . Slight coalescence of particles recognized.

× . . . Noticeable coalescence of particles recognized and external view of emulsified composition showed that composition was divided into two layers.

Emulsification Type of the Emulsified Composition

The emulsification type of the emulsified composition was judged by the conductometric method and a microscopic inspection.

Skin Irritation

The skin irritation was evaluated by the protein denaturation rate measuring method, as explained in detail hereafter.

Utilizing water system high performance liquid chromatography, the concentration of the solution of the surfactant used in the emulsified composition was adjusted to 10 mM with an egg albumen buffering solution, having a pH of 7 and the egg albumen denaturation rate was measured using an absorption peak of 220 nm.

$$\text{Denaturation rate} = \frac{(HO - HS) \times 100}{HO}$$

HO: height of 220 nm absorption peak of egg albumen

HS: height of 220 nm absorption peak when a sample was added to egg albumen

○ . . . egg albumen denaturation rate below 30%

Δ . . . egg albumen denaturation rate 30% or more, but less than 60%

× . . . egg albumen denaturation rate of 60% or more

The above evaluation results are shown in Table 1.

As is clear from the results set forth in Table 1, each of the emulsified compositions according to the examples of the present invention had a low protein denaturation rate (i.e., low skin irritation) and an excellent stability, and can cope with a wide range of required HLB of an oily substance.

Various oily substances from liquid paraffin, a non-polar oil with low HLB to 2-octyl dodecanol, a polar oil with a relatively high HLB, further including silicone oil, which is considered to be difficult to emulsify, can be easily emulsified.

Especially, in Examples 2 to 9, the weight proportion of a ampholytic surfactant and a higher fatty acid was within the range of from 0.5:9.5 to 9.5:0.5, and the emulsified compositions had a greater stability than those of Examples 10 and 11.

TABLE 1

|  |  | Example | | | | | | | | Comparative Example | | | Example | |
| --- | --- | --- | --- | --- | --- | --- | --- | --- | --- | --- | --- | --- | --- | --- |
|  |  | 2 | 3 | 4 | 5 | 6 | 7 | 8 | 9 | 1 | 2 | 3 | 10 | 11 |
| Oily substance | Liquid paraffin | 48.5 | 47.75 | 46.25 | 31 | — | — | 47.75 | 47.75 | 48.5 | 48.5 | 48.5 | 30 | 50 |
|  | Methyl polysiloxane | — | — | — | — | — | 30 | — | — | — | — | — | — | — |
|  | 2-Octyl dodecanol | — | — | — | — | 57.3 | — | — | — | — | — | — | — | — |
|  | Oleic acid | 1.5 | 3 | 6 | 4 | 3 | 3 | — | 3 | — | — | — | 0.02 | 3 |
|  | Stearic acid | — | — | — | — | — | — | 3 | — | 1.5 | 1.5 | 1.5 | — | — |
| Emulsifier | Betaine lauryldimethyl aminoacetate | — | — | — | — | — | — | 1.5 | — | — | — | — | — | — |
|  | Sodium 2-undecyl-N,N,N-(hydroxyethyl-Carboxymethyl)-2-imidazoline | 1.5 | 1.5 | 1.5 | O.6 | 1.5 | 1.5 | 1.5 | — | — | — | — | 3 | 0.02 |
|  | Sodium laurate | — | — | — | — | — | — | — | — | — | 1.5 | — | — | — |
|  | Sodium laurylsulfate | — | — | — | — | — | — | — | — | — | — | 1.5 | — | — |
|  | Polyoxyethylene hardened castor oil (EO-40) | — | — | — | — | — | — | — | — | — | — | 1.5 | — | — |
| Purified water |  | bal | bal | bal | bal | bal | bal | bal | bal | bal | bal | bal | bal | bal |
| *1 |  | 1 | 2 | 4 | 6.67 | 2 | 2 | 2 | 2 | — | — | — | 0.007 | 150 |
| Stability |  | ○ | ○ | ○ | ○ | ○ | ○ | ○ | ○ | × | × | Δ | Δ | Δ |

TABLE 1-continued

|  | Example | | | | | | | | Comparative Example | | | Example | |
| --- | --- | --- | --- | --- | --- | --- | --- | --- | --- | --- | --- | --- | --- |
|  | 2 | 3 | 4 | 5 | 6 | 7 | 8 | 9 | 1 | 2 | 3 | 10 | 11 |
| Emulsification Type | O/W | O/W | W/O/W | W/O/W | O/W | O/W | W/O | W/O | O/W | O/W | O/W | O/W | W/O |
| Protein Denaturation Rate (Skin Irritation) | ○ | ○ | ○ | ○ | ○ | ○ | ○ | ○ | x | x | Δ | ○ | ○ |

*1 (higher fatty acid) / (ampholytic and/or semi-polar surface active agent)(Wt. %)

Example 12

Hair cream consisting of the following formulating ingredients in the following formulating ratios was prepared, and the properties of the thus produced preparation were evaluated in the same way as in Example 2.

The hair cream was prepared in the following manner.

To an aqueous layer formed by dissolving lauryldimethylamine oxide, glycerol and methyl parabane in purified water were added an oil phase mixture consisting of fluid paraffin, oleic acid, cetyl-2-ethyl hexanoate, and an aromatic, while stirring in a homogenizer, whereby a hair cream was obtained.

| O/W type hair cream | |
| --- | --- |
| Formulating ingredients | Wt. % |
| Lauryldimethylamine oxide | 2.0 |
| Oleic acid | 2.0 |
| Liquid paraffin | 35.0 |
| Cetyl-2-ethylhexanoate | 3.0 |
| Glycerol | 5.0 |
| Perfume | 0.2 |
| Methyl parabene | 0.1 |
| Purified water | balance |

The hair cream thus prepared had an excellent stability and low skin irritation.

Example 13

A cleansing cream consisting of the following formulating ingredients in the following formulating ratios was prepared and evaluated in the same way as in Examples 2 to 11.

The cleansing cream was prepared by the following procedure.

To an aqueous phase formed by dissolving lauryldimethyl betaine aminoacetate, propylene glycol, methyl parabene, and butyl parabene in purified water was added an oil phase formed by melting stearic acid, fluid paraffin, cetanol, beeswax, spermaceti wax, lanolin, and perfume at a temperature of about 75° C., whereby a cleansing cream was obtained.

| O/W type cleansing cream | |
| --- | --- |
| Formulating ingredients | Wt. % |
| Lauryldimethyl betaine aminoacetate | 2.0 |
| Stearic acid | 2.0 |

| O/W type cleansing cream | |
| --- | --- |
| Formulating ingredients | Wt. % |
| Liquid paraffin | 28.0 |
| Cetanol | 2.0 |
| Beeswax | 2.0 |
| Spermaceti wax | 5.0 |
| Propylene glycol | 3.0 |
| Lanolin | 1.0 |
| Perfume | 0.2 |
| Methyl parabene | 0.1 |
| Butyl parabene | 0.1 |
| Purified water | balance |

The cleansing cream thus prepared had an excellent stability and safety.

Example 14

A cold cream consisting of the following formulating ingredients in the following formulating ratios was prepared, and evaluated in the same way as in Examples 2 to 10.

This cold cream was prepared by the following procedure.

An aqueous phase was added to an oil phase to obtain the cold cream.

| W/O type cold cream | |
| --- | --- |
| Formulating ingredients | Wt. % |
| 2-Undecyl-N,N,N-(hydroxyethylcarboxymethyl)-2-imidazoline sodium | 2.0 |
| Linoleic acid | 6.0 |
| Liquid paraffin | 25.0 |
| Lanolin alcohol | 4.0 |
| Beeswax | 15.0 |
| Paraffin wax | 5.0 |
| Borax | 0.8 |
| Perfume | 0.4 |
| Methyl parabene | 0.1 |
| Butyl parabene | 0.1 |
| Purified water | Balance |

The cold cream thus prepared had an excellent stability and low skin irritation.

Example 15

A hair mousse consisting of the following formulating ingredients in the following formulating ratios was prepared. This hair mousse was prepared by the following procedure.

To an aqueous phase formed by dissolving 2-undecyl-N,N,N-(hydroxyethylcarboxymethyl)-2-imidazoline sodium to a part of purified water was added an oily substance mixture consisting of oleic acid, polydimethylsiloxane, and isoparaffin, while agitation was continued with a homogenizer, and an O/W type emulsified composition was obtained. Thereafter, the emulsified composition thus obtained was added to an aqueous solution consisting of propylene glycol, cationic high molecular compound, perfume, ethanol, and the remainder water, these elements were mixed, and then the obtained mixture was measured into a can, and n-butane was filled in the can.

| O/W type hair mousse | |
|---|---|
| Formulating ingredients | Wt. % |
| 2-Undecyl-N,N,N-(hydroxyethylcarboxymethyl)-2-imidazoline sodium | 2.0 |
| Oleic acid | 2.0 |
| Polydimethyl siloxane | 2.0 |
| Isoparaffin | 8.0 |
| Propylene glycol | 3.0 |
| Cationic polymer | 0.1 |
| Perfume | q.s. |
| Ethanol | 10.0 |
| Purified water | balance |
| n-Butane | 10.0 |

The hair mousse according to the present example had an excellent stability and service properties, because the amount of surfactant required was about a half that of the conventional hair mousse, and the present hair mousse was not weighty. Also, the present hair mousse was more lustrous than the conventional mousse. The luster was evaluated by feeling. Furthermore, the present mousse had a low skin irritation.

Example 16

A hair mousse was prepared in the same way as in Example 15.

| O/W type hair mousse | |
|---|---|
| Formulating ingredients | Wt. % |
| Betaine lauryldimethylaminoacetate | 1.0 |
| Oleic acid | 0.1 |
| Isoparaffin | 0.1 |
| Silicone oil | 2.0 |
| Glycerol | 3.0 |
| Ampholytic polymer | 3.0 |
| Perfume | q.s. |
| Ethanol | 20.0 |
| Purified water | balance |
| n-Butane | 7.0 |

The hair mousse thus obtained had an excellent stability and low skin irritation.

Example 17

Hair spray consisting of the following formulating ingredients in the following formulating ratios was prepared.

This hair spray was prepared by the following procedure.

To an oil phase in which liquid paraffin and oleic acid were dissolved was added, while agitation was continued with a homogenizer, an aqueous phase in which sodium 2-undecyl-N,N,N-(hydroxyethylcarboxymethyl)-2-imidazoline were dissolved with a part of purified water, whereby a W/O type emulsified composition was obtained, and the composition thus obtained was filled in a can, and thereafter, a liquid mixture consisting of ethanol, perfume, anionic macromolecule and purified water was added to the composition, and a valve was mounted to the can, following which dimethyl ether was filled in the can, whereby the hair spray was obtained.

| W/O type hair spray | |
|---|---|
| Formulating ingredients | Wt. % |
| 2-Undecyl-N,N,N-(hydroxyethylcarboxymethyl)-2-imidazoline sodium | 0.08 |
| Oleic acid | 0.3 |
| Liquid paraffin | 2.4 |
| Ethanol | 10.0 |
| Perfume | q.s. |
| Anionic polymer | 3.0 |
| Dimethyl ether | 75.0 |
| Purified water | balance |

The hair spray thus prepared had an excellent stability and low skin irritation.

Example 18

To a system in which a part of purified water, stearyltrimethylammonium chloride, and cetanol were dissolved under stirring at a temperature of about 75° C., was added an O/W type emulsified composition obtained in the same way as in Example 12, whereby a hair rinse was obtained.

| Hair rinse | |
|---|---|
| Formulating ingredients | Wt. % |
| 2-Undecyl-N,N,N-(hydroxyethylcarboxymethyl)-2-imidazoline sodium | 0.2 |
| Oleic acid | 0.2 |
| Liquid paraffin | 1.0 |
| Cetyl-2-ethylhexanoate | 1.0 |
| Stearyltrimethylammonium chloride | 1.5 |
| Cetanol | 1.5 |
| Perfume | 0.2 |
| Metyl parabene | 0.1 |
| Purified water | remainder |

The thus prepared hair rinse had an excellent stability and low skin irritation.

Example 19

A W/O type emulsified enamel consisting of the following formulating ingredients in the following formulating ratios was prepared by the procedures mentioned below, and evaluated in the same way as in Examples 2 to 11.

A liquid mixture of acetyltriethyl citrate, n-butyl acetate, toluene, and isostearic acid (Emery #871: produced by Emery Co., Ltd.) was prepared, and to the mixture thus prepared were added nitrocellulose RS 1-4, an acrylic resin, sucrose benzoate, and camphor, and these were dissolved under agitation. Subsequently, a pigment and an organic modified bentonite were added to the solution obtained and dispersed under agitation. Subsequently, ethylhydroxyethylcellulose dissolved in ethanol and purified water containing Ovazoline 662-N and propylene glycohol were homogenously mixed, and the mixture obtained was added to the previously obtained dispersion, following which the newly obtained mixture was emulsified under agitation, whereby a red nail beautifying preparation was obtained.

| W/O type emulsified enamel | |
|---|---|
| Formulating ingredients | Wt. % |
| Ovazoline 662-N (produced by Toho Kagaku K.K.) [effective content 30%] | 1.7 |
| Isostearic acid (Emery #871: produced by Emery Co., Ltd.) | 2.0 |
| Purified water | 20.0 |
| Ethylhydroxyethylcellulose*1 | 0.5 |
| Propylene glycol | 2.0 |
| Nitrocellulose RS¼*2 | 14.0 |
| Acrylic resin*3 | 6.0 |
| Sucrose benzoate | 6.0 |
| Acetyltriethyl citrate | 6.0 |
| Camphor | 1.5 |
| n-Butyl acetate | 22.0 |
| Toluene | 15.0 |
| Pigment*4 | 1.0 |
| Organically modified bentonite*5 | 1.0 |
| Ethanol | 5.0 |

*1Mixed cellulose ether, most of the three OH groups in cellulose being replaced by an ethoxyl or ethylhydroxyl group, the 5% viscosity in toluene/95% ethanol (8:2) being 20 to 30 cps (25° C.)("EHEC-LOW": produced by Hercules Co., Ltd.)
*2Nitrocellulose with an isopropyl alcohol wetness of 30%; proxylin RS ¼(produced by Daisel Co., Ltd.)
*370:30 copolymer of butyl acrylate and methyl methacrylate, the molecular weight thereof being about 200, ("Oligen BM-3" produced by Matsumoto Seiyaku Kogyo K.K.)
*4Deeve Maloon/titanium dioxide (¼)
*5Distearyl chloride dimethylammonium hectorite The W/O type emulsified enamel thus obtained had an excellent stability and low skin irritation.

Example 20

An O/W type creamy foundation consisting of the following ingredients in the following formulating ratios was prepared by the procedure as mentioned below, and evaluated in the same way as in Examples 2 to 11.

To an aqueous phase consisting of Ovazoline 662-N, purified water, dynamite glycerol and p-methyl benzoic acid was added a powder phase consisting of kaolin, talc, titanium dioide, red iron oxide, yellow iron oxide, and black iron oxide, and emulsified under agitation was an oil phase consisting of propylene glycol, perfume, and isostearic acid ("Emery #871":produced by Emery Co. Ltd.), whereby an O/W type creamy foundation was obtained.

| O/W type creamy foundation | |
|---|---|
| Formulating ingredients | Wt. % |
| Ovazoline 662-N (produced by Toho Kagaku K.K.) [effective content 30%] | 7.5 |
| Purified water | 74.25 |
| Dynamite glycerin | 2.0 |

-continued

| O/W type creamy foundation | |
|---|---|
| Formulating ingredients | Wt. % |
| p-Methylbenzoic acid | 0.1 |
| Kaolin | 5.0 |
| Talc | 10.0 |
| Titanium dioxide | 2.0 |
| Red iron oxide | 0.2 |
| Yellow iron oxide | 0.8 |
| Black iron oxide | 0.05 |
| Propylene glycol | 3.0 |
| Perfume | 0.1 |
| Isostaeric acid (Emery #871: produced by Emery Co., Ltd.) | 0.25 |

The O/W type creamy foundation thus prepared had an excellent stability and low skin irritation.

Example 21

An O/W type creamy foundation consisting of the following ingredients in the following fomulating ratios was prepared by the procedure as mentioned below, and evaluated in the same way as in Examples 2 to 11.

To an aqueous phase consisting of Ovazoline 662-N, purified water, dynamite glycerol, p-methyl benzoic acid and 1,3-butylene glycol was added a powder phase consisting of talc, titanium dioide, red iron oxide, yellow iron oxide, and black iron oxide, and emulsified under agitation was an oil phase consisting of perfume, cyclic polysiloxane, and isostearic acid ("Emery #871": produced by Emery Co., Ltd.), whereby an O/W type creamy foundation was obtained.

| O/W type creamy foundation | |
|---|---|
| Formulating ingredients | Wt. % |
| Ovazoline 662-N (produced by Toho Kagaku K.K.) [effective content 30%] | 13.5 |
| Purified water | 65.35 |
| Dynamite glycerol | 2.0 |
| p-Methyl benzoic acid | 0.1 |
| 1,3-Butylene glycol | 3.0 |
| Talc | 13.65 |
| Titanium dioxide | 5.0 |
| Red iron oxide | 0.25 |
| Yellow iron oxide | 1.0 |
| Black iron oxide | 0.1 |
| Perfume | 0.05 |
| Cyclic polysiloxane | 5.0 |
| Isostearic acid (Emery #871: produced by Emery Co., Ltd.) | 0.45 |

The O/W type creamy foundation thus prepared had an excellent stability and low skin irritation.

Example 22

A W/O type creamy foundation consisting of the following ingredients in the following formulating ratios was prepared by the procedure as mentioned below, and evaluated in the same way as in Examples 2 to 11.

Into an oil phase consisting of a perfume, cyclic polysiloxane, and isostearic acid (Emery #871: produced by Emery Co., Ltd.) was emulsified under agitation an aqueous phase consisting of Ovazoline 662-N, purified water, dynamite glycerol, p-methyl benzoic acid, and 1,3-butylene glycol, and to the emulsion thus obtained was added a powder phase consisting of talc, titanium dioxide, red iron oxide, yellow iron oxide, and black iron oxide, whereby a W/O type creamy foundation was obtained.

W/O type creamy foundation

| Formulating ingredients | Wt. % |
|---|---|
| Ovazoline 662-N (produced by Toho Kagaku K.K.) [effective content 30%] | 1.5 |
| Purified water | 65.35 |
| Dynamite glycerol | 2.0 |
| p-Methylbenzoic acid | 0.1 |
| 1,3-Butylene glycol | 3.0 |
| Talc | 13.65 |
| Titanium dioxide | 5.0 |
| Red iron oxide | 0.25 |
| Yellow iron oxide | 1.0 |
| Black iron oxide | 0.1 |
| Perfume | 0.06 |
| Cyclic polysiloxane | 5.0 |
| Isostearic acid (Emery #871: produced by Emery Co., Ltd.) | 4.05 |

The W/O type creamy foundation thus prepared had an excellent stability and low skin irritation.

Example 23

A high internal aqueous phase W/O type cream consisting of the following ingredients in the following formulating ratios was prepared by the procedure as mentioned below, and evaluated in the same way as in Examples 2 to 11.

Into an oil phase consisting of isoparaffin, dimethyl polysiloxane, liquid paraffin, cetyl octanoate, methyl phenyl polysiloxane, ethyl parabene, and isostearic acid (Emery #871: produced by Emery Co., Ltd.) was emulsified under agitation an aqueous phase consisting of Ovazoline 662-N, dynamite glycerol, 1,3-butylene glycol, and purified water, whereby a high internal aqueous phase W/O type cream was obtained.

High internal aqueous phase W/O type creamy foundation

| Formulating ingredients | Wt. % |
|---|---|
| Ovazoline 662-N (produced by Toho Kagaku K.K.) [effective content 30%] | 4.0 |
| Dynamite glycerol | 5.0 |
| 1,3-Butylene glycol | 5.0 |
| Isoparaffin | 2.0 |
| Dimethyl polysiloxane | 1.0 |
| Liquid paraffin | 1.0 |
| Cetyl isooctanoate | 1.0 |
| Methyl phenyl polysiloxane | 1.0 |
| Ethyl parabene | 0.1 |
| Purified water | balance |
| Isostearic acid (Emery #871: produced by Emery Co., Ltd.) | 3.0 |

The high internal aqueous phase W/O type cream thus prepared had an excellent stability and low skin irritation.

Example 24

A W/O type hair cream consisting of the following ingredients in the following formulating ratios was prepared by the procedure as mentioned below, and evaluated in the same way as in Examples 2 to 11.

Into an oil phase consisting of isoparaffin, dimethyl polysiloxane 20cs, dimethyl polysiloxane (polymerization degree: 1000), vitamin E acetate, and isostearic acid (Emery #871: produced by Emery Co., Ltd.) was emulsified under agitation an aqueous phase consisting of Ovazoline 662-N, distearyldimethylammonium chloride, a perfume, purified water, polyethylene glycol 6000, methyl parabene, keratin hydrolyzate, lecithin, and smecton, whereby a W/O type hair cream was obtained.

W/O type hair cream

| Formulating ingredients | Wt. % |
|---|---|
| Isoparaffin | 20.0 |
| Dimethyl polysiloxane 20 cs | 2.0 |
| Dimethyl polysiloxane (polymerization degree 1000) | 5.0 |
| Distearyldimethylammonium chloride | 0.8 |
| Ovazoline 662-N (produced by Toho Kagaku K.K.) [effective content 30%] | 1.6 |
| Vitamin E acetate | 0.1 |
| Isostearic acid (Emery #871: produced by Emery Co., Ltd.) | 3.0 |
| Perfume | q.s. |
| Purified water | balance |
| Polyethylene glycol 6000 | 1.0 |
| Glycerol | 5.0 |
| Methyl parabene | 0.2 |
| Keratin hydrolyzate | 0.05 |
| Smecton | 1.2 |
| Lecithin | 0.05 |

The W/O type hair cream thus prepared had an excellent stability and low skin irritation.

Example 25

An O/W type hair mousse consisting of the following ingredients in the following formulating ratios was prepared by the procedure as mentioned below, and evaluated in the same way as in Examples 2 to 11.

To an aqueous phase formed by dissolving Ovazoline 662-N, collagen hydrolyzate, and lecithin with a part of purified water was added under agitation an oil phase consisting of isostearic acid (Emery #871: produced by Emery Co., Ltd.), dimethyl polysiloxane (polymerization degree: 5000), and isoparaffin, whereby an O/W type hair mousse was obtained. The hair mousse thus obtained was added to an aqueous solution of purified water containing a perfume, ethanol, and methyl parabene, and mixed therein. The obtained mixture was measured into a can, and n-butane was filled into the can.

O/W type hair mousse

| Formulating ingredients | Wt. % |
|---|---|
| Ovazoline 662-N (produced by Toho Kagaku K.K.) [effective content 30%] | 2.0 |
| Collagen hydrolyzate | 0.05 |
| Lecithin | 0.05 |
| Isostearic acid (Emery #871: produced by | 1.0 |

-continued

| O/W type hair mousse | |
|---|---|
| Formulating ingredients | Wt. % |
| Emery Co., Ltd.) | |
| Dimethyl polysiloxane (polymerization degree 5000) | 4.0 |
| Isoparaffin | 12.0 |
| Propylene glycol | 5.0 |
| Perfume | q.s. |
| Ethanol | 10.0 |
| Methyl parabene | 0.2 |
| Purified water | balance |
| n-Butane | 10.0 |

The hair mousse thus prepared had an excellent stability and low skin irritation. In addition, this hair mousse exhibited usabilities similar to those of a W/O type mousse, although the present mousse was an O/W type, and provided a gentle and soft hair dressing.

Example 26

A W/O type creamy mascara consisting of the following formulating ingredients in the following formulating ratios was prepared by the procedure as mentioned below, and evaluated in the same way as in Examples 2 to 11.

An oil phase portion consisting of isoparaffin, solid paraffin wax, beeswax, polyisoprene resin, isostearic acid (Emery #875: produced by Emery Co., Ltd.), and polyacrylic ester emulsion was heated to a temperature of 70° C., and stirred to be homogenized. An aqueous phase portion consisting of purified water, methyl parabene, perfume, organically modified bentonite, and Ovazoline 662-N was heated to a temperature of 70° C., and added to the oil phase portion, to be emulsified, whereafter the mixture thus emulsified was cooled and filled into a mascara vessel.

| W/O type creamy mascara | |
|---|---|
| Formulating ingredients | Wt. % |
| Isoparaffin | 30.0 |
| Solid paraffin wax | 3.0 |
| Beeswax | 3.0 |
| Polyisoprene resin | 3.0 |
| Isostearic acid (Emery #875: produced by Emery Co., Ltd.) | 2.5 |
| Purified water | 20.0 |
| Polyacrylic ester emulsion | 30.0 |
| Methyl parabene | 0.05 |
| Perfume | q.s. |
| Organically modified bentonite (produced by National Lead Corporation) | 2.0 |
| Ovazoline 662-N (Toho Kagaku K.K.) [effective content 30%] | 3.3 |

This W/O type creamy mascara thus prepared had an excellent stability and low skin irritation.

Example 27

An O/W type body rinse consisting of the following formulating ingredients in the following formulating ratios was prepared by the procedure as mentioned below, and evaluated in the same way as in Examples 2 to 11.

To an aqueous phase consisting of ethanol, 1,3-butylene glycol, Ovazoline 662-N, KOH, methyl prabene, xanthan gum, carboxyvinyl polymer, and purified water was added a powder phase consisting of mica-filled titanium, and an oil phase consisting of methyl polysiloxane, dimethyl polysiloxane—polyethlene glycol, isostearic acid (Emery #875: produced by Emery Co., Ltd.), and polyoxypropylene (9 mol) diglyceryl ether was emulsified into the obtained mixture under agitation, whereby an O/W type body rinse was obtained.

| O/W type body rinse | |
|---|---|
| Formulating ingredients | Wt. % |
| Methyl polysiloxane | 4.0 |
| Dimethyl polysiloxane polyethylene glycol (EO 24 mol) | 4.0 |
| Ethanol | 1.0 |
| 1,3-Butylene glycol | 20.3 |
| Ovazoline 662-N (produced by Toho Kagaku K.K.) [effective content 30%] | 10.0 |
| Isostearic acid ("Emery #875": produced by Emery Co., Ltd.) | 1.0 |
| Polyoxypropylene (9 mol) diglyceryl ether | 10.0 |
| Mica-filled titanium | 0.2 |
| KOH | 0.25 |
| Methyl parabene | 0.1 |
| Xanthan gum | 0.5 |
| Carboxyvinyl polymer | 0.5 |
| Purified water | balance |

The O/W type body rinse thus prepared had an excellent stability and low skin irritation.

Example 28

A W/O type emulsified enamel consisting of the following formulating ingredients in the following formulating ratios was prepared according to Example 11, and evaluated in the same way as in Examples 2 to 11.

| W/O type emulsified enamel | |
|---|---|
| Formulating ingredients | Wt. % |
| Lebon 2000 (produced by Sanyo Kasei K.K.) [effective content 30%] | 1.7 |
| Linoleic acid | 2.0 |
| Purified water | 20.0 |
| Ethylhydroxyethylcellulose[*1] | 0.5 |
| Propylene glycol | 2.0 |
| Nitrocellulose RS ¼[*2] | 14.0 |
| Acrylic resin[*3] | 6.0 |
| Sucrose benzoate | 8.0 |
| Acetyltriethyl citrate | 6.0 |
| Camphor | 1.5 |
| n-Butyl acetate | 22.0 |
| Toluene | 15.0 |
| Pigment[*4] | 1.0 |
| Organically modified bentonite[*5] | 1.0 |
| Ethanol | 5.0 |

[*1]Cellulose ether mixture, many of the three OH groups in cellulose being replaced by an ethoxyl group or an ethylhydroxyl group, 5% viscosity thereof in toluene/95% ethanol (8:2) being 20 to 30 cps (EHEC-LOW: produced by Hercules Co., Ltd.)
[*2]Nitrocellulose with isopropyl alcohol wetness of which is 30%; pyroxylin RS ¼(produced by Daisel Co., Ltd.)

-continued

| W/O type emulsified enamel | |
|---|---|
| Formulating ingredients | Wt. % |

*³70:30 copolymer of butyl acrylate and methyl methacrylate, the molecular weight being about 2000, ("Oligen" BM-3: Matsumoto Seiyaku Kogyo K.K.)
*⁴Dieve maloon/titanium dioxide (⁴⁄₁)
*⁵Stearyldimethylbenzylammoniumhectrite chloride The W/O type emulsified enamel thus prepared had an excellent stability and low skin irritation.

Example 29

An O/W type creamy foundation consisting of the following ingredients in the following formulating ratios was prepared by the procedure as described below, and evaluated in the same way as in Examples 2 to 11.

To an aqueous phase consisting of Ronzain-CS, purified water, dynamite glycerin, and p-methylbenzoic acid was added a powder phase consisting of kaolin, talc, titanium dioxide, red iron oxide, yellow iron oxide, and black iron oxide, and an oil phase consisting of propylene glycol, perfume, and linolenic acid was emulsified therein under agitation, whereby an O/W type creamy foundation was obtained.

| O/W type creamy foundation | |
|---|---|
| Formulating ingredients | Wt. % |
| Ronzain-CS (produced by Ronza Co., Ltd.) [effective content 50%] | 4.5 |
| Purified water | 74.25 |
| Dynamite glycerol | 2.0 |
| p-Methylbenzoic acid | 0.1 |
| Kaolin | 5.0 |
| Talc | 10.0 |
| Titanium dioxide | 2.0 |
| Red iron oxide | 0.2 |
| Yellow iron oxide | 0.8 |
| Black iron oxide | 0.05 |
| Propylene glycol | 3.0 |
| Perfume | 0.1 |
| Linolenic acid | 0.25 |

The O/W type creamy foundation thus prepared had an excellent stability and low skin irritation.

Example 30

An O/W type creamy foundation consisting of the following ingredients in the following formulating ratios was prepared by the procedure as mentioned below, and evaluated in the same way as in Examples 2 to 11.

To an aqueous phase consisting of Ronzain-CS, purified water, dynamite glycerin, p-methylbenzoic acid, and 1,3-butylene glycol was added a powder phase consisting of talc, titanium dioxide, red iron oxide, yellow iron oxide, and black iron oxide, and an oil phase consisting of perfume, cyclicpolysiloxane and lauric acid was emulsified therein under agitation, whereby an O/W type creamy foundation was obtained.

| O/W type creamy foundation | |
|---|---|
| Formulating ingredients | Wt. % |
| Ronzain-CS (produced by Ronza Co., Ltd.) [effective content 50%] | 8.0 |
| Purified water | 65.35 |
| Dynamite glycerol | 2.0 |
| p-Methylbenzoic acid | 0.1 |
| 1,3-Butylene glycol | 3.0 |
| Talc | 13.65 |
| Titanium dioxide | 5.0 |
| Red iron oxide | 0.25 |
| Yellow iron oxide | 1.0 |
| Black iron oxide | 0.1 |
| Perfume | 0.05 |
| Cyclic polysiloxane | 5.0 |
| Lauric acid | 0.45 |

The O/W type creamy foundation thus prepared had an excellent stability and low skin irritation.

Example 31

A W/O type creamy foundation consisting of the following ingredients in the following formulating ratios was prepared by the procedure as mentioned below, and evaluated in the same way as in Examples 2 to 11.

An aqueous phase consisting of Unisafe A-LM, purified water, dynamite glycerol, p-methylbenzoic acid, and 1,3-butylene glycol, which aqueous phase was formed by adding a powder phase consisting of talc, titanium dioxide, red iron oxide, yellow iron oxide, and black iron oxide, to an oil phase consisting of perfume, cyclic polysiloxane and stearic acid, and was emulsified under agitation, whereby an O/W type creamy foundation was obtained.

| W/O type creamy foundation | |
|---|---|
| Formulating ingredients | Wt. % |
| Unisafe A-LM (produced by Nihon Yushi K.K.) [effective content 30%] | 1.5 |
| Purified water | 65.3 |
| Dynamite glycerol | 2.0 |
| p-Methylbenzoic acid | 0.1 |
| 1,3-Butylene glycol | 3.0 |
| Talc | 13.65 |
| Titanium dioxide | 5.0 |
| Red iron oxide | 0.25 |
| Yellow iron oxide | 1.0 |
| Black iron oxide | 0.1 |
| Perfume | 0.05 |
| Cyclic polysiloxane | 5.0 |
| Stearic acid | 4.05 |

The W/O type creamy foundation thus prepared had an excellent stability and low skin irritation.

Example 32

A high internal aqueous phase W/O type cream consisting of the following formulating ingredients in the following formulating ratios was prepared by the procedure as mentioned below, and evaluated in the same way as in Examples 2 to 11.

Into an oil phase consisting of isoparaffin, dimethyl polysiloxane, liquid paraffin, cetyl isooctanoate, methyl phenyl polysiloxane, ethyl parabene, and stearic acid was emulsified under agitation an aqueous phase consisting of Anon BDF, dynamite glycerol, 1,3-butylene glycol, and purified water, whereby a high internal aqueous phase W/O type cream was obtained.

High internal aqueous phase W/O type cream

| Formulating ingredients | Wt. % |
|---|---|
| Anon BDF (produced by Nihon Yushi K.K.) [effective content 30%] | 5.0 |
| Dynamite glycerol | 5.0 |
| 1,3-Butylene glycol | 5.0 |
| Isoparaffin | 2.0 |
| Dimethyl polysiloxane (6cps) | 1.0 |
| Liquid paraffin | 1.0 |
| Cetyl isooctanoate | 1.0 |
| Methyl phenyl polysiloxane (6cps) | 1.0 |
| Ethyl parabene | 0.1 |
| Purified water | balance |
| Stearic acid | 3.0 |

The high internal aqueous phase W/O type cream thus prepared had an excellent stability and low skin irritation.

Example 33

A W/O type hair cream consisting of the following formulating ingredients in the following formulating ratios was prepared by the procedure as mentioned below, and evaluated in the same way as in Examples 2 to 11.

Into an oil phase consisting of isoparaffin, dimethyl polysiloxane (polymerization degree 1000), Miratine CBS, vitamin E acetate, and palmitic acid was emulsified under agitation an aqueous phase consisting of distearyldimethylammonium chloride, perfume, purified water, polyethylene glycol 6000, glycerol, methyl parabene, keratin hydrolyzate, and smecton, whereby a W/O type hair cream was obtained.

W/O type hair cream

| Formulating ingredients | Wt. % |
|---|---|
| Isoparaffin | 20.0 |
| Dimethyl polysiloxane 20cs | 2.0 |
| Dimethyl polysiloxane (polymerization degree 1000) | 5.0 |
| Distearyldimethylammonium chloride | 0.8 |
| Miratain CBS (produced by Miranol Co., Ltd.) [effective content 50%] | 3.0 |
| Vitamin E acetate | 0.1 |
| Palmitic acid | 3.0 |
| Perfume | q.s. |
| Purified water | balance |
| Polyethylene glycol 6000 | 1.0 |
| Glycerol methyl parabene | 5.0 |
| Methyl parabene | 0.2 |
| Keratin hydrolyzate | 0.1 |
| Smecton | 1.2 |

The W/O type hair cream thus prepared had an excellent stability and low skin irritation.

Example 34

An O/W type hair mousse consisting of the following formulating ingredients in the following formulating ratios was prepared by the procedure as described below, and evaluated in the same way as in Examples 2 to 11.

To an aqueous phase formed by dissolving Dehainton AB-30 in a part of purified water was added, while agitation was continued, an oil phase consisting of 12-hydroxystearic acid, dimethyl polysiloxane (polymerization degree: 5000), and isoparaffin, whereby an O/W type hair mousse was obtained. Subsequently, the hair mousse thus obtained was added to and mixed and with an aqueous solution of purified water containing perfume, ethanol, and methyl parabene. The mixture obtained was measured into a can, and n-butane was filled into the can.

O/W type hair mousse

| Formulating ingredients | Wt. % |
|---|---|
| Dehainton AB-30 (produced by Henkel) [effective content 30%] | 6.7 |
| 12-Hydroxystearic acid | 1.0 |
| Dimethyl polysiloxane (polymerization degree: 5000) | 4.0 |
| Isoparaffin | 12.0 |
| Propylene glycol | 5.0 |
| Perfume | q.s. |
| Ethanol | 10.0 |
| Methyl parabene | 0.2 |
| Purified water | balance |
| n-Butane | 10.0 |

The O/W type hair mousse thus prepared had an excellent stability and low skin irritation. In addition, this hair mousse exhibited service properties similar to those of a W/O type hair mousse, although an O/W type, and provided gentle and soft hair dressing.

Example 35

A hair treatment was obtained in the same manner as in Example 14.

Hair treatment

| Formulating ingredients | Wt. % |
|---|---|
| Anon CBS (produced by Nihon Yushi K.K.) [effective content 30%] | 4.0 |
| Isostearic acid ("Emery #875": produced by Emery Co., Ltd.) | 3.0 |
| Stearyltrimethylammonium chloride | 0.5 |
| Isoparaffin | 3.0 |
| Squalan | 0.5 |
| 2-Octyldodecanol | 0.5 |
| Dimethyl polysiloxane (polymerization degree: 5000) | 0.2 |
| Cetanol | 0.5 |
| Organically modified bentonite* | 0.3 |
| Perfume | 0.2 |
| Methyl parabene | 0.1 |
| Glycerol | 2.0 |
| 1.3-Butylene glycol | 1.0 |
| Purified water | balance |

*stearyldimethylbenzylammoniumhectolite chloride

The hair treatment thus prepared made the hair glossy, and had a hair setting ability, although a W/O type, and had an excellent stability and low skin irritation.

Example 36

A W/O type creamy mascara consisting of the following formulating ingredients in the following formulating ratios was prepared by the procedure as mentioned below, and evaluated in the same way as in Examples 2 to 11.

An oil phase portion consisting of isoparaffin, solid paraffin wax, beeswax, polyisoprene resin, isostearic acid ("Emery #875": produced by Emery Co., Ltd.), and polyacrylic ester emulsion was heated to a temperature of 70° C., and agitated to be homogenized. An aqueous phase portion consisting of purified water, methyl parabene, perfume, organic modified bentonite, and Anon GLM was heated to a temperature of 70° C., and added to the oil phase portion to be emulsified, and thereafter, the emulsified product obtained was cooled and filled in a mascara vessel.

| W/O type creamy mascara | |
|---|---|
| Formulating ingredients | Wt. % |
| Isoparaffin | 30.0 |
| Solid paraffin wax | 3.0 |
| Beeswax | 3.0 |
| Polyisoprene resin | 3.0 |
| Isostearic acid ("Emery #875": Produced by Emery Co., Ltd.) | 3.0 |
| Purified water | 20.0 |
| Polyacrylic ester emulsion | 30.0 |
| Methyl parabene | 0.05 |
| Perfume | q.s. |
| Organically modified bentonite (produced by National Lead Corporation) | 2.0 |
| Anon GLM (produced by Nihon Yushi K.K.) [effective content 30%] | 3.3 |

The W/O type creamy mascara thus prepared had an excellent stability and low skin irritation.

Example 37

An O/W type body rinse consisting of the following formulating ingredients in the following formulating ratios was prepared by the procedure as described below, and evaluated in the same way as in Examples 2 to 11.

To an aqueous phase consisting of ethanol, 1,3-butylene glycol, Ovazoline 662-N, KOH, methyl parabene, xanthan gum, carboxyvinyl polymer, and purified water was added a powder phase consisting of mica-filled titanium, and further, emulsified under agitation was an oil phase consisting of methyl polysiloxane, dimethyl polysiloxane—polyethylene glycol, isostearic acid ("Emery #875":produced by Emery Co., Ltd.), and polyoxypropylene (9 mol) diglyceryl ether, whereby an O/W type body rinse was obtained.

| O/W type body rinse | |
|---|---|
| Formulating ingredients | Wt. % |
| Methyl polysiloxane | 4.0 |
| Dimethyl polysiloxane polyethylene glycol (EO 24 mols) | 4.0 |
| Ethanol | 1.0 |
| 1,3-Butylene glycol | 20.0 |
| Wandamin OX-100 (produced by Shin Nihon Rika K.K.) [effective content 35%] | 8.6 |
| Isostearic acid ("Emery #875 ": produced by Emery Co., Ltd.) | 1.0 |
| Polyoxypropylene (9 mol) diglyceryl ether | 10.0 |
| Mica-filled titanium | 0.2 |

-continued

| O/W type body rinse | |
|---|---|
| Formulating ingredients | Wt. % |
| KOH | 0.25 |
| Methyl parabene | 0.1 |
| Xanthan gum | 0.5 |
| Carboxyvinyl polymer | 0.5 |
| Purified water | balance |

The O/W type body rinse thus prepared had an excellent stability and low skin irritation.

Examples 38 and 39

Emulsified compositions consisting of the formulating ingredients set forth in Table 2, respectively, in the formulating ratios also set forth in Table 2, were prepared, and the influences of clay minerals upon an emulsified system examined. The results are set forth in Table 2.

TABLE 2

| | Example 38 | Example 39 |
|---|---|---|
| Ovazoline 662-N (produced by Toho Kagaku K.K.) | 5.0 | 5.0 |
| Isostearic acid "Emery #875" (produced by Emery Co., Ltd.) | 3.0 | 3.0 |
| Dynamite glycerol | 5.0 | 5.0 |
| 1,3-Butylene glycol | 5.0 | 5.0 |
| Decamethylcyclopentasiloxane | 4.0 | 4.0 |
| Ethyl parabene | 0.1 | 0.1 |
| *Organically modified bentonite | — | 0.3 |
| Purified water | 83.9 | 83.6 |
| Stability | Storable for one month at room temperature | Storable for 6 months at room temperature and for a further 2 months at 50° C. |

*Distearyldimethylammoniumhectorite chloride

As shown in the table, it has been found that the emulsified composition of Example 39, which is formed by adding distearyldimethylammoniumhectlite chloride to the emulsified composition of Example 38, has an excellent long term stability, and even under more severe conditions (50° C.), the emulsification system consisting of the emulsified composition of Example 39 is noticeably stable.

APPLICABILITY IN INDUSTRY

As explained in detail in the foregoing, according to the present invention there is provided a novel complex displaying an excellent emulsification of even an oily substance with a wide range of required HLB, capable of easily controlling the emulsion type, and of forming a stable and low skin irritation emulsified composition.

According to the present invention, there can be also provided an emulsified composition, which can be easily produced even if an oily substance with a wide range of required HLB, having an excellent stability, and displaying a low irritation of the skin.

Therefore, the emulsified composition according to the present invention may be used effectively as an emulsifier in a wide range of industrial fields, such as cosmetics, medicines, agricultural chemicals, releasing agents, water repellents, emulsion fuels, and emulsion polymerization, etc.

What is claimed is:

1. A fatty acid amphoteric surfactant complex obtained by mixing a) at least one imidazolinium ampholytic surfactant of the formula:

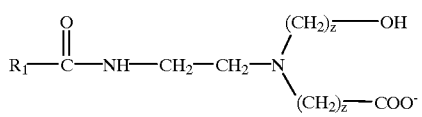

wherein $R_1$ represents an alkyl or alkenyl group having 9 to 17 carbon atoms on average; and Z is 1 or 2;

with b) a higher fatty acid selected from the group consisting of oleic acid, isostearic acid and a mixture of oleic acid and isostearic acid;

wherein the ratio of said higher fatty acid to the total amount of said imidazolinium ampholytic surfactant(s) in said complex ranges from about 25:75 to 90:10.

2. A complex according to claim 1, further comprising 0.01 to 5% by weight of a clay mineral.

3. A complex according to claim 2, wherein the clay mineral is at least one clay mineral selected from the group consisting of montmorillonite, zaconte, nontronite, saponite, hectorite, vermiculite, beagum, bentonite, silicate, fluorosilicate, magnesium aluminum silicate, and synthetic hectorite (laponite).

4. A complex according to claim 2, wherein the clay mineral is an organic modified clay obtained by treating a clay mineral with a quaternary ammonium cationic surface active agent.

5. A complex according to claim 2, wherein the clay mineral is present in an amount of from about 0.1% to about 2% by weight.

6. A complex according to claim 1, wherein said higher fatty acid is oleic acid.

7. A complex according to claim 1, wherein said higher fatty acid is isostearic acid.

8. A complex according to claim 1 wherein said higher fatty acid is a mixture of oleic acid and isostearic acid.

9. An emulsion comprising a liquid, an oily ingredient and a complex according to claim 1.

10. An emulsion comprising a liquid, an oily ingredient and a complex according to claim 2.

11. An emulsion comprising a liquid, an oily ingredient and a complex according to claim 3.

12. An emulsion comprising a liquid, an oily ingredient and a complex according to claim 4.

13. An emulsion comprising a liquid, an oily ingredient and a complex according to claim 5.

14. An emulsion comprising a liquid, an oily ingredient and a complex according to claim 6.

15. The emulsion according to claim 14, which is an oil-in-water emulsion.

16. The emulsion according to claim 14, which is a water-in-oil emulsion.

17. An emulsion comprising a liquid, an oily ingredient and a complex according to claim 7.

18. The emulsion according to claim 17, which is an oil-in-water emulsion.

19. The emulsion according to claim 17, which is a water-in-oil emulsion.

20. An emulsion comprising a liquid, an oily ingredient and a complex according to claim 8.

21. The emulsion according to claim 20, which is an oil-in-water emulsion.

22. The emulsion according to claim 20, which is a water-in-oil emulsion.

* * * * *

UNITED STATES PATENT AND TRADEMARK OFFICE
CERTIFICATE OF CORRECTION

PATENT NO.    : 6,323,246 B1
DATED         : November 27, 2001
INVENTOR(S)   : Yasunari Nakama et al.

It is certified that error appears in the above-identified patent and that said Letters Patent is hereby corrected as shown below:

<u>Title page,</u>
Item [56], References Cited, FOREIGN PATENT DOCUMENTS,
change "1 548 948  12/1967 (JP)" to -- 1 548 948  12/1967 (FR --

Signed and Sealed this

Second Day of September, 2003

JAMES E. ROGAN
*Director of the United States Patent and Trademark Office*